US009730727B2

(12) United States Patent
Sato (10) Patent No.: US 9,730,727 B2
(45) Date of Patent: Aug. 15, 2017

(54) PUNCTURE TREATMENT TOOL (71) Applicant: OLYMPUS CORPORATION, Tokyo (JP)

(72) Inventor: Masatoshi Sato, Tokyo (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 15/193,926

(22) Filed: Jun. 27, 2016

(65) Prior Publication Data

US 2016/0302824 A1 Oct. 20, 2016

Related U.S. Application Data (63) Continuation of application No. PCT/JP2015/068862, filed on Jun. 30, 2015.

(30) Foreign Application Priority Data

Jun. 30, 2014 (JP) ................................. 2014-133914

(51) Int. Cl.
A61B 17/00 (2006.01)
A61B 17/34 (2006.01)
(Continued)

(52) U.S. Cl.
CPC ............... A61B 17/34 (2013.01); A61B 1/00 (2013.01); A61B 10/02 (2013.01); A61B 10/04 (2013.01);
(Continued)

(58) Field of Classification Search
CPC .......... A61B 10/02; A61B 2017/00393; A61B 5/151; A61B 5/1405; A61B 5/1411
See application file for complete search history.

(56) References Cited

U.S. PATENT DOCUMENTS

2009/0043258 A1* 2/2009 Fujisaki ............ A61M 25/0084
604/164.01
2011/0224575 A1* 9/2011 Carrillo, Jr. ........ A61B 10/0233
600/566

FOREIGN PATENT DOCUMENTS

JP H09-103433 A 4/1997
JP 2005-523741 A 8/2005
(Continued)

OTHER PUBLICATIONS

Sep. 1, 2015 International Search Report issued in Patent Application No. PCT/JP2015/068862.
(Continued)

Primary Examiner — Julie A Szpira
(74) Attorney, Agent, or Firm — Oliff PLC (57) ABSTRACT A puncture treatment tool includes a needle tube whose distal end is insertable into tissue, a cylindrical main body through which the needle tube is inserted, a needle stopper through which the main body is inserted and which is provided such that a position where the needle stopper is fixed to the main body can be changed in a direction of a longitudinal axis of the main body, and a slider which is fixed to a proximal end part of the needle tube, the slider being disposed to be operated movable relative to the main body. The slider is configured to be capable of selecting from a first state in which the slider is movable in the axial direction relatively to the main body without rotating in the circumferential direction of the main body, or a second state in which the slider is rotatable in the circumferential direction.

7 Claims, 5 Drawing Sheets (51) Int. Cl.
  *A61B 1/00* (2006.01)
  *A61B 10/02* (2006.01)
  *A61B 10/04* (2006.01)
  *A61B 17/29* (2006.01)

(52) U.S. Cl.
  CPC .... *A61B 17/00234* (2013.01); *A61B 17/3478* (2013.01); *A61B 2010/045* (2013.01); *A61B 2017/00296* (2013.01); *A61B 2017/00331* (2013.01); *A61B 2017/00389* (2013.01); *A61B 2017/00393* (2013.01); *A61B 2017/2929* (2013.01); *A61B 2017/3413* (2013.01)

(56) References Cited

FOREIGN PATENT DOCUMENTS

| | | |
|---|---|---|
| JP | 2006-180939 A | 7/2006 |
| JP | 2012-200487 A | 10/2012 |
| WO | 03/088833 A1 | 10/2003 |
| WO | 2011/112357 A1 | 9/2011 |
| WO | 2012/102099 A1 | 8/2012 |

OTHER PUBLICATIONS

Mar. 1, 2016 Notice of Allowance issued in Japanese Patent Application No. 2015-560884.

\* cited by examiner

PUNCTURE TREATMENT TOOL

This application is a continuation application based on a PCT International Application No. PCT/JP2015/068862, filed on Jun. 30, 2015, whose priority is claimed on Japanese Patent Application No. 2014-133914, filed on Jun. 30, 2014. The contents of both the PCT International Application and the Japanese Patent Application are incorporated herein by reference.

BACKGROUND OF THE INVENTION

Field of the Invention

The present invention relates to a puncture treatment tool, and more specifically, to a puncture treatment tool used for procedures, such as biopsy.

Description of Related Art

In the related art, a procedure of inserting treatment tools having a needle tube into a treatment tool insertion channel of an endoscope or the like and puncturing a lesion to sample tissue is performed. Pathological observation using a microscope or the like is performed on the sampled tissue, and various kinds of diagnosis are performed. Such examination is generally referred to as a biopsy.

Japanese Unexamined Patent Application, First Publication No. H9-103433 describes a puncturing needle operation assisting device for an endoscope that is used for such a procedure. This assisting device includes an overtube and a puncturing needle so as to be movable forward and backward within the overtube, and a distal end of the puncturing needle enters and leaves a distal end of the overtube when the puncturing needle is operated to move forward and backward on a proximal side.

SUMMARY OF THE INVENTION

According to a first aspect of the present invention, a puncture treatment tool includes a needle tube whose distal end is insertable into tissue; a cylindrical main body through which the needle tube is inserted; a needle stopper through which the main body is inserted and which is provided such that a position where the needle stopper is fixed to the main body can be changed in a direction of a longitudinal axis of the main body; and a slider which is fixed to a proximal end part of the needle tube, the slider being disposed to be operated movable relative to the main body at a position more proximal to the main body than the needle stopper in an axial direction of the needle tube, and a relative movement range of the slider with respect to the main body being determined by abutting against the needle stopper. The slider is configured to be capable of selecting from a first state in which the slider is movable in the axial direction relative to the main body without rotating in a circumferential direction of the main body, or a second state in which the slider is rotatable in the circumferential direction relative to the main body is selectable.

According to a second aspect of the invention, in the puncture treatment tool according to the first aspect, in the second state, the slider is configured so as to relatively move in the axial direction while rotating in the circumferential direction.

According to a third aspect of the invention, in the puncture treatment tool according to the first aspect, a third state in which the slider and the main body are not engaged with each other is selectable besides the first state and the second state.

According to a fourth aspect of the invention, in the puncture treatment tool according to the second aspect, a third state in which the slider and the main body are not engaged with each other is selectable besides the first state and the second state.

According to a fifth aspect of the invention, in the puncture treatment tool according to the first aspect, an outer circumferential surface of a region in the main body on which the slider slides may include a first groove that extends straight in the direction of the longitudinal axis of the main body, and a second groove that extends helically around the longitudinal axis of the main body, and the slider may include a protruding part which protrudes toward the main body and is selectively engageable with one of the first groove and the second groove. The first state may be a state in which the slider is movable straight with respect to the main body when the protruding part and the first groove are engaged with each other, and the second state may be a state in which the slider is movable forward with respect to the main body while rotating around the longitudinal axis of the main body when the protruding part and the second groove are engaged with each other.

According to a sixth aspect of the invention, in the puncture treatment tool according to the fifth aspect, the main body may include a separating part that separates into the first groove and the second groove.

According to a seventh aspect of the invention, in the puncture treatment tool according to the first aspect, the slider may include a switch that switches between the first state and the second state.

DETAILED DESCRIPTION OF THE INVENTION

A first embodiment of the invention will be described with reference to FIGS. 1 to 3.

Figure 1:
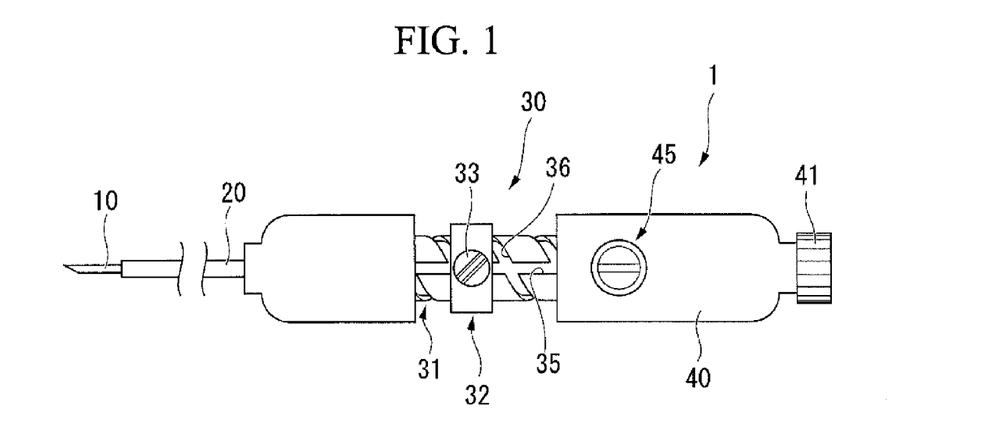
FIG. 1 is a view showing a puncture treatment tool according to a first embodiment of the invention.

FIG. 1 is a view showing a puncture treatment tool 1 of the present embodiment. The puncture treatment tool 1 is used by being inserted through a treatment tool channel of a flexible endoscope. The puncture treatment tool 1 includes a needle tube 10, a flexible sheath 20, and an operation section 30. The needle tube 10 is provided to be inserted into tissue. The flexible sheath 20 is provided to be inserted through by the needle tube 10. The operation section 30 is provided on a proximal end side of the needle tube 10 and the sheath 20.

The needle tube 10 is formed in a tubular shape, using metallic materials, such as stainless steel, nickel titanium, and cobalt chromium. The distal end of the needle tube 10 is sharply formed and can be inserted into tissue.

The sheath 20 is formed in an elongated tubular shape, using resin, a closely wound metal coil, or the like.

The operation section 30 includes a main body 31, and a slider 40. The main body 31 is provided that a proximal end part of the sheath 20 is fixed to the main body 31. The main body 31 is formed in a tubular shape. The slider 40 is provided that a proximal end part of the needle tube 10 is fixed to the slider 40. The slider 40 is also formed in a substantially tubular shape, and when a proximal end side of the main body 31 enters the slider 40, the slider 40 is attached so as to be movable relative to the main body 31.

After the needle tube 10 protrudes out of the proximal end of the sheath 20, the needle tube extends to the inside of the slider 40 through the inside of the main body 31, and is fixed to the slider 40. Therefore, by moving the slider 40 relative to the main body 31, the needle tube 10 can be moved relative to the main body 31 and the sheath 20, and thus the distal end of the needle tube 10 can be moved into and out of the distal end of the sheath 20.

A needle stopper 32 that determines the relative movement range of the slider 40 is attached to the main body 31, and the slider 40 can be moved until the slider comes into contact with the needle stopper 32. Accordingly, the maximum amount of protrusion of the needle tube 10 from the sheath 20 is determined. Since the needle stopper 32 becomes movable with respect to the main body 31 if an operation knob 33 provided to protrude is grasped and loosened, and the needle stopper is fixed to the main body 31 if the needle stopper 32 is fastened, the maximum amount of protrusion of the needle tube 10 can be adjusted by changing the position where the needle stopper 32 is fixed to the main body 31.

A plug 41 of a stylet (not shown) inserted through the needle tube 10 is attached to a proximal end part of the slider 40. The stylet can be inserted into the slider 40 from an opening formed in a position at the proximal end part of the slider 40, and can be extracted from and inserted into the needle tube 10. The stylet inserted through the needle tube 10 prevents foreign matter from entering the needle tube 10 until being extracted, and is extracted when tissue is sampled.

A linear first groove 35 that extends in a longitudinal direction of the main body 31, that is, an axial direction of the needle tube 10, and a helical second groove 36 are formed in an outer circumferential surface on a proximal-end-side region of the main body 31 that enters and leaves the slider 40. The first groove 35 and the second groove 36 are formed with a depth such that both of the grooves do not communicate with an internal space of the main body 31 and are bottomed grooves.

The slider 40 is provided with a switch 45 that switches aspects of the movement of the slider 40 relative to the main body 31. As shown in FIG. 2, the switch 45 is attached to a through-hole 46 formed in the outer circumferential surface of the slider 40, and a wire spring 47 is attached to the switch 45. The wire spring 47 protrudes in a substantially circular-arc shape toward the main body 31 that has entered the slider 40, and can selectively enter the first groove 35 or the second groove 36. Since an extending direction of a knob 45a, an extending direction of the wire spring 47, and the like that are provided in the switch 45 coincide with each other, a user can know the direction of the wire spring within the slider 40 by viewing the switch 45.

The operation of the puncture treatment tool 1 configured as above when being used will be described.

First, the user inserts the endoscope into the inside of a patient's body, and introduces a distal end part of the endoscope to the vicinity of the tissue, which is a procedure target, as preparatory work before use. As the endoscope, well-known ones, such as an optical endoscope and an ultrasonic endoscope, can be variously selected according to target tissue, the position of a puncturing part, and the like.

Next, the distal end of the puncture treatment tool 1 is inserted into the treatment tool channel of the endoscope from a treatment tool channel port provided in the endoscope operation section. At this time, the slider 40 is moved (moved backward) in a direction away from the distal end of the puncture treatment tool 1 with respect to the main body 31 and the distal end of the needle tube 10 is housed within the sheath 20 so that an inner wall of the treatment tool channel is not damaged. Thereafter, the puncture treatment tool 1 is moved forward within the treatment tool channel, and the sheath 20 is made to protrude from a distal end opening of the treatment tool channel.

If the slider 40 is moved (moved forward) in a direction approaching the distal end of the puncture treatment tool 1 with respect to the main body 31, the needle tube 10 protrudes from the sheath 20, and is brought into an insertable state into tissue. In the puncture treatment tool 1, by operating the switch 45, the engagement aspect between the main body 31 and the slider 40 can be switched, and aspects when the needle tube 10 is moved forward and backward can be selected.

Figure 2:
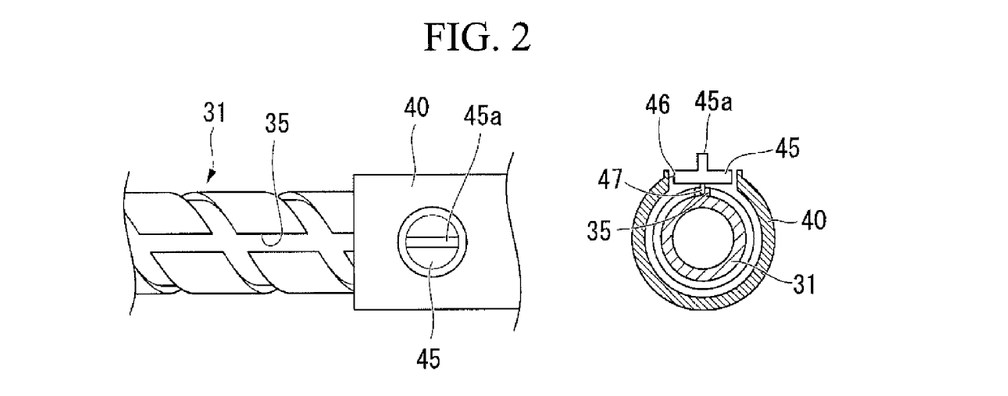
FIG. 2 is a view showing a main body and a slider in a first state.

As shown in FIG. 2, although the slider 40 is movable in the axial direction of the needle tube 10 in the first state where the wire spring 47 has entered the first groove 35, the slider does not substantially rotate in a circumferential direction of the main body 31 formed in a tubular shape. Therefore, if the slider 40 is relatively moved in the axial direction of the needle tube 10, the needle tube 10 is moved forward and backward without rotating with respect to the sheath 20.

Figure 3:
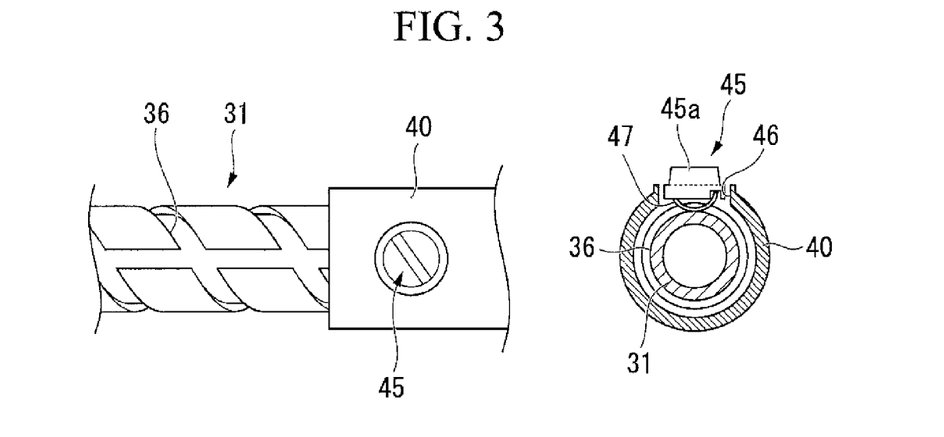
FIG. 3 is a view showing the main body and the slider in a second state.

Meanwhile, as shown in FIG. 3, a relative movement of the slider 40 in the axial direction of the needle tube 10 is definitely accompanied with a rotation of the slider 40 in a circumferential direction of the main body 31, in the second state where the wire spring 47 has entered the second groove 36. That is, unless the slider 40 rotates in the circumferential direction of the main body 31 in the second state, the slider 40 is not moved forward and backward with respect to the sheath 20. Therefore, the user can move the needle tube forward and backward while the needle tube 10 is reliably rotated by rotating the slider 40 in the circumferential direction of the main body 31.

The user can switch between the first state and the second state at any time by operating the switch 45. When the switch 45 is operated, a substantially circular-arc portion of the wire spring 47 is deformed so as to approach the switch 45, protrudes out from one groove of the first groove 35 and the second groove 36, then enters the other groove, and returns to the shape before deformation.

As described above, according to the puncture treatment tool 1 of the present embodiment, either of the first groove 35 and the second groove 36 formed in the main body 31, and the slider 40 can be engaged with each other via the wire spring 47 by operating the switch 45. Accordingly, the needle tube 10 can be operated by reliably and suitably using the first state where the needle tube 10 is moved forward and backward without rotation and the second state where the needle tube 10 is moved forward and backward with rotation, and a puncturing procedure can be suitably selected depending on the properties of tissue, or the like.

Next, a second embodiment of the invention will be described with reference to FIGS. 4 to 10. A difference between the present embodiment and the first embodiment is the structure of the operation section. In addition, in the following description, components common to components already described will be designated by the same reference numerals, and a redundant description will be omitted.

Figure 4:
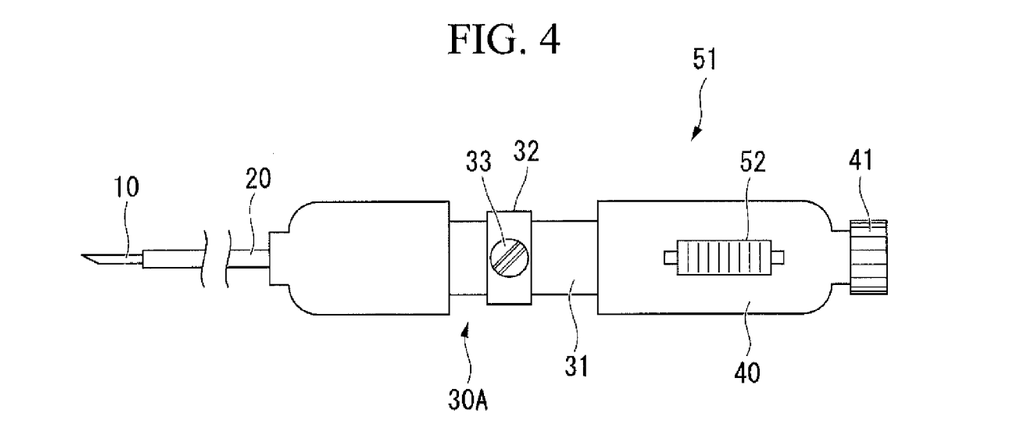
FIG. 4 is a view showing a puncture treatment tool according to a second embodiment of the invention.

FIG. 4 is a view showing a puncture treatment tool 51 of the present embodiment. Instead of the above-described switch 45, a slide-type switch 52 is attached to the slider 40 of an operation section 30A.

Figure 5:
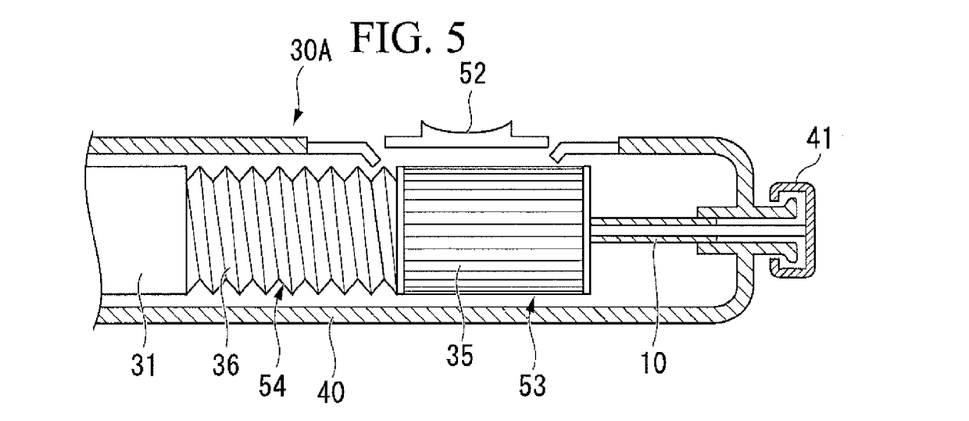
FIG. 5 is a partial sectional view showing an operation section of the puncture treatment tool according to the second embodiment of the invention.

FIG. 5 is a partial sectional view showing the operation section 30A. A first region 53 where a plurality of the first grooves 35 are formed side by side in the circumferential direction of the main body 31, and a second region 54 where only the second groove 36 is formed are provided on the proximal end side of the main body 31. The first region 53 and the second region 54 are provided side by side in the axial direction of the main body 31, and the first grooves 35 and the second groove 36 are provided so as not to overlap each other in the axial direction of the main body 31.

Figure 6:
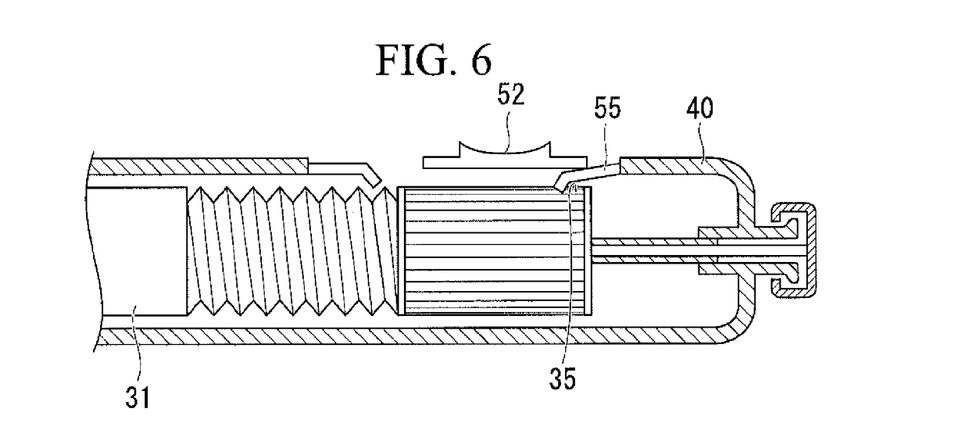
FIG. 6 is a view showing the operation section in the first state.
Figure 7:
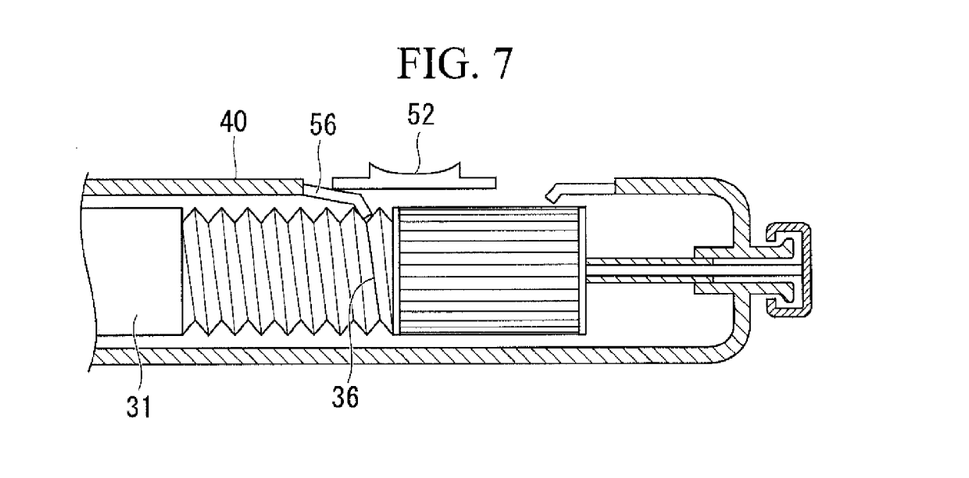
FIG. 7 is a view showing the operation section in the second state.

If the switch 52 is moved to the proximal end side of the puncture treatment tool 51, as shown in FIG. 6, a first claw 55 provided in the slider 40 is pushed by the switch 52 and approaches the main body 31, and is engaged with one of the first grooves 35. If the switch 52 is moved to the distal end side of the puncture treatment tool 51, as shown in FIG. 7, a second claw 56 provided in the slider 40 is pushed by the switch 52 and approaches the main body 31, and is engaged with the second groove 36. Therefore, the first state where the slider 40 and the main body 31 are engaged with each other via the first grooves 35, and the second state where the slider 40 and the main body 31 are engaged with each other via the second groove 36 can be reliably switched by moving the switch 52 through sliding operation.

The slider 40 is provided with a locking part (not shown), and the first state or the second state is held by the switch 52 being engaged with the locking part.

As shown in FIG. 5, when the switch 52 is at an intermediate position between a position in a first state and a position in the second state, the switch is brought into a third state where the slider 40 and the main body 31 are not engaged with each other. In this state, the slider 40 is movable forward and backward with respect to the main body 31, and the rotation of the slider 40 with respect to the main body 31 is not restricted.

Although the operation of the puncture treatment tool 51 when being used is almost the same as that of the first embodiment, particularly in a case where there is no need for restriction on the rotation involved in the forward and backward movement of the needle tube 10, it is also possible to perform a procedure in the third state.

Even in the puncture treatment tool 51 of the present embodiment, similar to the first embodiment, the needle tube 10 can be operated by reliably and suitably using the first state and the second state, and a procedure can be suitably performed.

Additionally, by operating the switch 52, the third state that is not any one of the first state and the second state can be realized.

Moreover, since the plurality of first grooves 35 are provided in the first region 53, there are many variations in the relative positional relationship in the circumferential direction between the sheath and the needle tube in the first state. As a result, the direction or the like of the distal end of the needle tube 10 can be finely adjusted.

In addition, since the first grooves and the second groove are provided in the different regions, the switching between the first state and the second state can be smoothly performed.

A modification example of the present embodiment will be described with reference to FIGS. 8 to 10. In this modification example, the needle tube cannot be moved forward and backward with respect to the main body and the sheath in the second state.

Figure 8:
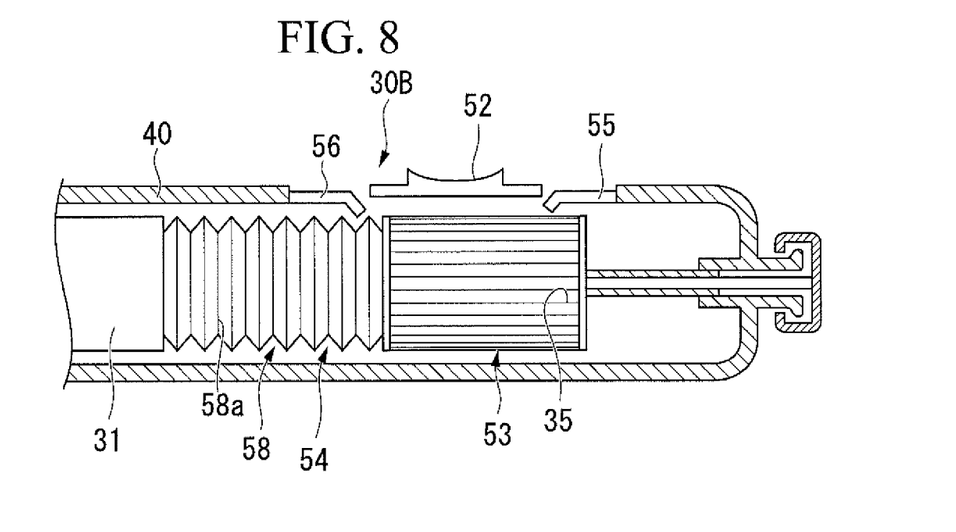
FIG. 8 is a partial sectional view showing the operation section of the puncture treatment tool related to a modification example of the second embodiment of the invention.
Figure 9:
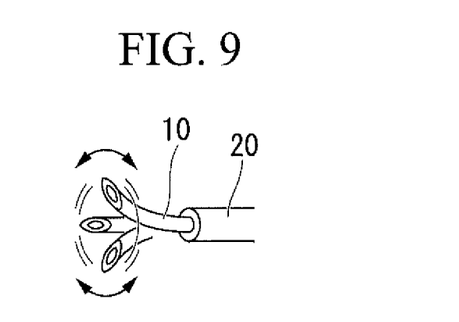
FIG. 9 is a view showing the movement of a needle tube in the second state of the modification example.

FIG. 8 shows an operation section 30B of a modification example in a partial section. A second groove 58 formed in the second region 54 is formed by a plurality of annular unit grooves 58a being provided side by side in the axial direction of the main body 31. Therefore, although the slider 40 that is engaged with one of the unit grooves 58a and brought into the second state is rotatable in the circumferential direction of the main body 31, the slider cannot be moved forward and backward with respect to the main body 31.

If the puncture treatment tool of the modification example is used, for example, the following procedure is possible.

First, bending is imparted to the distal end of the needle tube 10. Although the needle tube 10 deforms substantially straight within the sheath 20, the needle tube returns to its initial shape of which the distal end is bent if the needle tube protrudes from the sheath 20. Therefore, a shape memory alloy such as nickel titanium is suitable as a material for the needle tube 10. If the main body 31 and the slider 40 are brought into the second state, using the shape memory alloy as the material for the needle tube 10, as shown in FIG. 9, the direction of the distal end of the needle tube 10 can be adjusted to a desired direction by rotating the needle tube 10 without moving the needle tube forward and backward.

Figure 10:
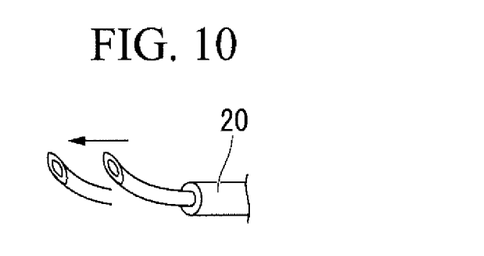
FIG. 10 is a view showing the movement of the needle tube in the first state of the modification example.

If the direction of the distal end is adjusted to the desired direction and if the main body 31 and the slider 40 are brought into the first state, as shown in FIG. 10, the needle tube 10 can be moved forward and backward while suitably holding the direction of the distal end. By appropriately combining such operations, it becomes easy to perform puncturing at a desired position or to efficiently perform puncturing in a plurality of places within a certain range.

While the puncture treatment tool of the invention has been described above using the respective embodiments, the technical scope of the invention is not limited to the above embodiments. Combinations of constituent elements can be changed, various alternations can be added to the respective constituent elements, or omissions can be made, without departing from the concept of the invention.

Additionally, the invention is not to be considered as being limited by the foregoing description, and is limited only by the scope of the appended claims.

For example, in the invention, there is no particular limitation on the number of first grooves formed in the main body. Since the variations in the relative positional relationship in the circumferential direction between the sheath and the needle tube in the first state increase as the number of first grooves is increased, fine adjustment of the direction of the distal end of the needle tube is possible. However, in the first embodiment, the switching between the first state and the second state becomes less easy as the number of first grooves increases. Therefore, groove depths may be changed if necessary in the first groove and the second groove.

Additionally, although an example in which the slider is engaged with the groove provided in the main body has been described in the above-described embodiments, the engagement aspect between the main body and the slider is not limited to this. For example, the concavo-convex relationship between both of the main body and the slider may be reversed, for example, by providing a groove in the switch and engaging the groove with a protrusion on the main body.

Moreover, the puncture treatment tool of the invention may be appropriately provided with a mechanism provided with a well-known puncture treatment tool. For example, a lure lock or the like may be provided on the distal end part of the main body so as to be capable of being fixed to the treatment tool channel port of the endoscope. In this case, if the rotational direction of the lure lock when being fastened and the rotational direction of the slider when the slider is moved forward in the second state are made the same, the main body does not easily slip off from the treatment tool channel port when the needle tube is operated to move forward, which is preferable. In this case, if the slider and the main body are brought into the first state when the needle tube is moved backward, the main body does not easily slip off from the treatment tool channel port even when the needle tube is moved backward.

Additionally, the sheath slider may be provided and the sheath may be configured to be movable forward and backward with respect to the operation section.

Figure 11:
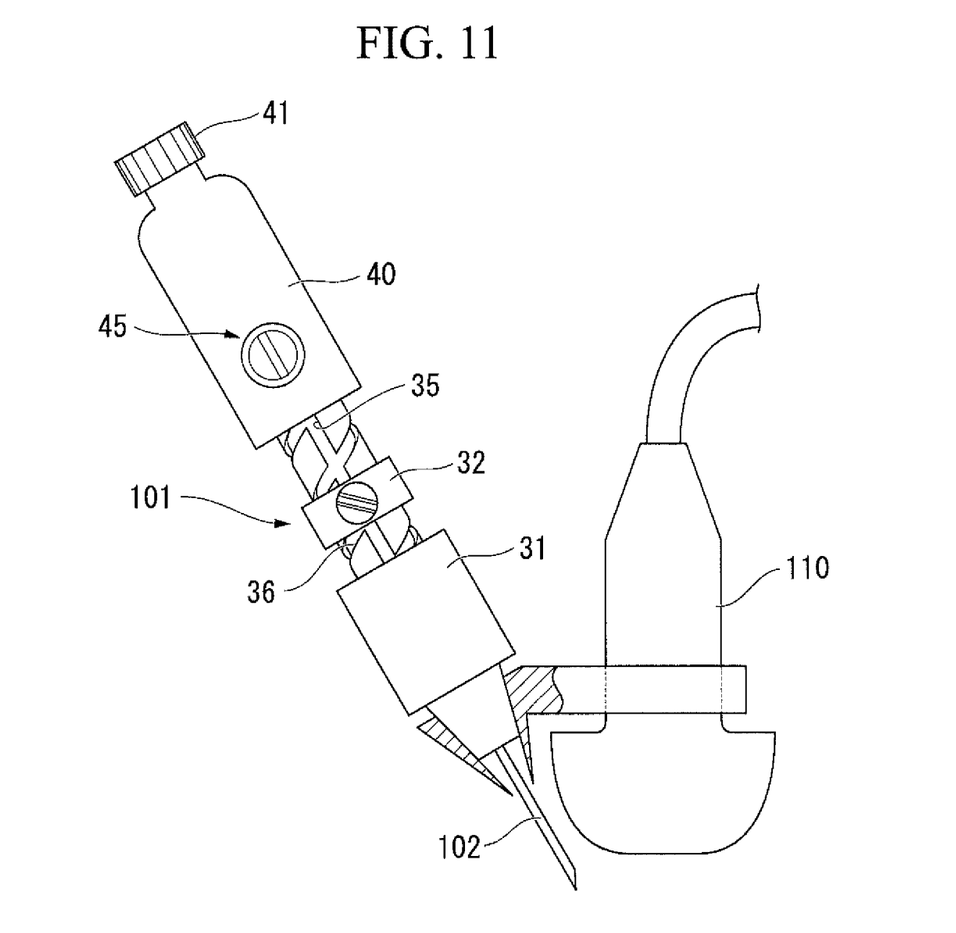
FIG. 11 is a view showing the puncture treatment tool according to the modification example of the invention.

In addition, the puncture treatment tool of the invention is not limited to that inserted into the endoscope. A puncture treatment tool 101 of a modification example of the invention shown in FIG. 11 can be used for puncturing or biopsy on a body surface by being combined with an ultrasonic probe 110 brought into contact with the body surface. In the puncture treatment tool 101, a certain degree of rigidity is required for the needle tube. Thus, a hard needle tube 102 having no flexibility or having a low flexibility is used. Additionally, since the treatment tool is not inserted into the endoscope, the treatment tool is configured without including the sheath. Even in such a configuration, almost the same effects as the respective above-described embodiments are exhibited.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A puncture treatment tool comprising:
a needle tube having a distal end that is insertable into tissue;
a flexible sheath through which the needle tube is inserted; and
an operation section disposed at a proximal end side of the needle tube and the sheath, the operation section including:
a cylindrical main body to which a proximal end part of the sheath is fixed, and through which a proximal end part of the needle tube is inserted;
a needle stopper through which the main body is inserted, the needle stopper being provided such that a position where the needle stopper is fixed to the main body changes in a direction of a longitudinal axis of the main body, the needle stopper including a knob configured to selectively shift between a first state in which the needle stopper is freely movable relative to the main body and a second state in which the needle stopper is fixed to the main body; and
a slider fixed to the proximal end part of the needle tube that protrudes from the proximal end part of the sheath, the slider being movable relative to the main body at a position more proximal to the main body than the needle stopper in an axial direction of the needle tube, and a relative movement range of the slider with respect to the main body being determined by abutting against the needle stopper, the slider including a switch configured to selectively switch between: (i) a first state in which the slider is movable in the axial direction relative to the main body without rotating in a circumferential direction of the main body, and (ii) a second state in which the slider is rotatable in the circumferential direction relative to the main body.

2. The puncture treatment tool according to claim 1, wherein in the second state, the slider is configured so as to relatively move in the axial direction while rotating in the circumferential direction.

3. The puncture treatment tool according to claim 2, wherein the switch of the slider is configured to selectively switch to a third state in which the slider and the main body are not engaged with each other.

4. The puncture treatment tool according to claim 1, wherein the switch of the slider is configured to selectively switch to a third state in which the slider and the main body are not engaged with each other.

5. The puncture treatment tool according to claim 1, wherein:
an outer circumferential surface of a region in the main body on which the slider slides includes: (i) a first groove that extends straight in the direction of the longitudinal axis of the main body, and (ii) a second groove that extends helically around the longitudinal axis of the main body;
the slider includes a protruding part which protrudes toward the main body and is selectively engageable with one of the first groove and the second groove; and
wherein the first state is a state in which the slider is movable straight with respect to the main body when the protruding part and the first groove are engaged with each other, and the second state is a state in which the slider is movable forward with respect to the main body while rotating around the longitudinal axis of the main body when the protruding part and the second groove are engaged with each other.

6. The puncture treatment tool according to claim 5, wherein the main body includes a separating part that separates into the first groove and the second groove.

7. The puncture treatment tool according to claim 1, wherein the switch is positioned more proximal than the knob with respect to the main body.

* * * * *